United States Patent
Speck et al.

(10) Patent No.: US 10,046,092 B2
(45) Date of Patent: *Aug. 14, 2018

(54) COATING FORMULATIONS FOR SCORING OR CUTTING BALLOON CATHETERS

(71) Applicant: AngioScore, Inc., Colorado Springs, CO (US)

(72) Inventors: Ulrich Speck, Berlin (DE); Madeleine Caroline Berg, Berlin (DE)

(73) Assignee: The SPECTRANETICS CORPORATION, Colorado Springs, CO (US)

( * ) Notice: Subject to any disclaimer, the term of this patent is extended or adjusted under 35 U.S.C. 154(b) by 39 days.

This patent is subject to a terminal disclaimer.

(21) Appl. No.: 14/731,715

(22) Filed: Jun. 5, 2015

(65) Prior Publication Data

US 2015/0297797 A1    Oct. 22, 2015

Related U.S. Application Data

(63) Continuation of application No. 13/975,209, filed on Aug. 23, 2013, now Pat. No. 9,078,951, which is a continuation of application No. 13/628,608, filed on Sep. 27, 2012, now Pat. No. 9,011,896, which is a continuation of application No. PCT/EP2010/066754, filed on Nov. 3, 2010.

(30) Foreign Application Priority Data

Apr. 19, 2010    (EP) .................................... 10160347

(51) Int. Cl.
| | |
|---|---|
| *A61F 2/00* | (2006.01) |
| *A61L 29/08* | (2006.01) |
| *A61L 29/16* | (2006.01) |
| *A61L 31/16* | (2006.01) |
| *A61M 25/10* | (2013.01) |
| *A61B 17/3207* | (2006.01) |
| *A61L 29/14* | (2006.01) |

(52) U.S. Cl.
CPC ...... *A61L 29/08* (2013.01); *A61B 17/320725* (2013.01); *A61L 29/143* (2013.01); *A61L 29/16* (2013.01); *A61L 31/16* (2013.01); *A61M 25/10* (2013.01); *A61M 25/104* (2013.01); *A61B 2017/320733* (2013.01); *A61L 2300/216* (2013.01); *A61L 2300/416* (2013.01); *A61L 2300/606* (2013.01); *A61L 2300/802* (2013.01); *A61M 2025/105* (2013.01); *A61M 2025/109* (2013.01)

(58) Field of Classification Search
None
See application file for complete search history.

(56) References Cited

U.S. PATENT DOCUMENTS

| | | | |
|---|---|---|---|
| 5,199,951 | A | 4/1993 | Spears |
| 5,304,121 | A | 4/1994 | Sahatjian |
| 5,370,614 | A | 12/1994 | Amundson et al. |
| 5,571,523 | A | 11/1996 | Lee et al. |
| 5,893,840 | A | 4/1999 | Hull et al. |
| 6,211,247 | B1 | 4/2001 | Goodman |
| 6,299,604 | B1 | 10/2001 | Ragheb et al. |
| 6,306,166 | B1 | 10/2001 | Barry et al. |
| 6,419,692 | B1 | 7/2002 | Yang et al. |
| 6,616,650 | B1 | 9/2003 | Rowe |
| 6,730,064 | B2 | 5/2004 | Ragheb et al. |
| 7,108,684 | B2 | 9/2006 | Farnan |
| 7,445,792 | B2 | 11/2008 | Toner et al. |
| 7,445,795 | B2 | 11/2008 | Bakhshaee et al. |
| 7,803,149 | B2 | 9/2010 | Bates et al. |
| 7,811,622 | B2 | 10/2010 | Bates et al. |
| 7,875,284 | B2 | 1/2011 | Reyes et al. |
| 7,955,350 | B2 | 6/2011 | Konstantino et al. |
| 8,673,387 | B2 | 3/2014 | Bates et al. |
| 8,721,667 | B2 | 5/2014 | Konstantino et al. |
| 8,864,743 | B2 | 10/2014 | Konstantino et al. |
| 9,011,896 | B2 * | 4/2015 | Speck et al. ................. 424/423 |
| 9,072,812 | B2 * | 7/2015 | Speck et al. |
| 9,078,951 | B2 * | 7/2015 | Speck et al. |
| 9,173,977 | B2 | 11/2015 | Speck et al. |

(Continued)

FOREIGN PATENT DOCUMENTS

| | | |
|---|---|---|
| CN | 1688350 A | 10/2005 |
| CN | 101610798 A | 12/2009 |

(Continued)

OTHER PUBLICATIONS

Cremers et al. Comparison of Two Different Paclitaxel-Coated Balloon Catheters in the Porcine Coronary Restenosis Model; Clin Res Cardiol (2009) 98:325-350; DOI 10.1007/s00392-009-0008-2.
EP Examination Report dated Oct. 9, 2013 from corresponding EP Application No. 10775805.4, 6 pages.
International Search Report and Written Opinion issued in PCT Application No. PCTEP2010066754 dated May 1, 2011, 11 pages.
Notification of the First Office Action dated Jan. 16, 2014, from corresponding Chinese Application No. 201080066293.3.
Scheller et al. Paclitaxel Balloon Coating, a Novel Method for Prevention and Therapy of Restenosis; Circulation. 2004;110:810-814, Aug. 9, 2004.

(Continued)

*Primary Examiner* — Hasan Ahmed

(57) ABSTRACT

The present invention is related to scoring or cutting balloon catheters carrying at least on a portion of their surface at least one oxidation-insensitive drug or oxidation-insensitive polymer-free drug preparation and at least one lipophilic antioxidant at a ratio of 3-100% by weight of the at least one lipophilic antioxidant in relation to 100% by weight of the drug, wherein the at least one oxidation-insensitive drug is selected of taxanes, thalidomide, statins, corticoids and lipophilic derivatives of corticoids, and the at least one lipophilic antioxidant is selected of nordihydroguaiaretic acid, resveratrol and propyl gallate.

15 Claims, No Drawings

(56) References Cited

U.S. PATENT DOCUMENTS

| | | |
|---|---|---|
| 9,770,536 B2 | 9/2017 | Speck et al. |
| 2002/0037358 A1 | 3/2002 | Barry et al. |
| 2004/0106975 A1 | 6/2004 | Solovay et al. |
| 2005/0037048 A1* | 2/2005 | Song .................... 424/423 |
| 2005/0278021 A1 | 12/2005 | Bates et al. |
| 2006/0020243 A1 | 1/2006 | Speck et al. |
| 2006/0240014 A1 | 10/2006 | Sukhatme |
| 2006/0259005 A1 | 11/2006 | Konstantino et al. |
| 2007/0020380 A1 | 1/2007 | Ding |
| 2007/0037739 A1 | 2/2007 | Wang et al. |
| 2007/0128242 A1 | 6/2007 | Zhao |
| 2007/0190103 A1 | 8/2007 | Hossainy et al. |
| 2007/0212394 A1 | 9/2007 | Reyes et al. |
| 2008/0021385 A1 | 1/2008 | Barry et al. |
| 2008/0118544 A1 | 5/2008 | Wang |
| 2008/0181927 A1 | 7/2008 | Zhao |
| 2008/0241215 A1 | 10/2008 | Falotico et al. |
| 2009/0136560 A1 | 5/2009 | Bates et al. |
| 2009/0246252 A1 | 10/2009 | Arps et al. |
| 2009/0246253 A1 | 10/2009 | Ding |
| 2010/0209472 A1* | 8/2010 | Wang .................... 424/423 |
| 2010/0233228 A1 | 9/2010 | Speck |
| 2010/0233236 A1 | 9/2010 | Zhao |
| 2010/0278997 A1 | 11/2010 | Speck et al. |
| 2010/0285085 A1 | 11/2010 | Stankus et al. |
| 2010/0324645 A1 | 12/2010 | Stankus et al. |
| 2011/0054396 A1 | 3/2011 | Kangas et al. |
| 2011/0143014 A1 | 6/2011 | Stankus et al. |
| 2011/0196340 A1 | 8/2011 | Barry et al. |
| 2011/0230818 A1 | 9/2011 | Kunis |
| 2011/0295200 A1 | 12/2011 | Speck et al. |
| 2012/0172787 A1 | 7/2012 | McClain et al. |
| 2012/0239001 A1 | 9/2012 | Barry et al. |
| 2013/0023817 A1 | 1/2013 | Speck et al. |
| 2013/0041315 A1 | 2/2013 | Speck |
| 2013/0046237 A1 | 2/2013 | Speck et al. |
| 2013/0231638 A1 | 9/2013 | Speck et al. |
| 2014/0257181 A1 | 9/2014 | Speck |
| 2016/0095960 A1 | 4/2016 | Speck et al. |
| 2017/0340778 A1 | 11/2017 | Speck et al. |

FOREIGN PATENT DOCUMENTS

| | | |
|---|---|---|
| JP | 2008504059 A | 5/2005 |
| JP | 2005343897 A | 12/2005 |
| WO | 1994023787 A1 | 10/1994 |
| WO | WO1994023787 A1 | 10/1994 |
| WO | 2002076509 A2 | 10/2002 |
| WO | 2004022124 A1 | 3/2004 |
| WO | 2004028582 A1 | 4/2004 |
| WO | 2004108130 A1 | 12/2004 |
| WO | 2006007173 A1 | 1/2006 |
| WO | 2009018816 A2 | 2/2009 |
| WO | 2009066330 A1 | 5/2009 |
| WO | 2009155405 A1 | 12/2009 |
| WO | 2011131259 A1 | 10/2011 |

OTHER PUBLICATIONS

Suzuki et al. Anti-Oxidants for Therapeutic Use: Why Are Only a Few Drugs in Clinical Use? Advanced Drug Delivery Reviews, vol. 61, 2009, pp. 287-289.

* cited by examiner

COATING FORMULATIONS FOR SCORING OR CUTTING BALLOON CATHETERS

CROSS REFERENCE TO RELATED APPLICATIONS

This application is a continuation of U.S. patent application Ser. No. 13/975,209, filed Aug. 23, 2013, which is a continuation of U.S. patent application Ser. No. 13/628,608, filed Sep. 27, 2012, which is a continuation of PCT Application No. PCT/EP2010/066754, filed Nov. 3, 2010, which claims the benefit of EP Application No. 10160347.0, filed Apr. 19, 2010, the full disclosures of each of which are incorporated herein by reference in their entirety.

BACKGROUND

1. Field of the Invention

The invention relates to the transfer of a drug loosely adhering to the surface of a scoring or cutting balloon catheter to a site inside the body, usually in a diseased blood vessel. The preferred application is local drug therapy during percutaneous transluminal angioplasty (PTA) or percutaneous transluminal coronary angioplasty (PTCA). The interventions are performed to restore blood flow in stenotic or occluded blood vessels, usually into arteries. A catheter is introduced in a major artery. At the distal end the catheter carries a cylindrical balloon in folded state with very small diameter and additional tools or structures which scratch or cut the luminal surface of the treated blood vessel or tissue. In the folded state the balloon can enter or pass the stenotic or occluded segment of e.g. a blood vessel. Once positioned in the narrowed segment, the balloon is inflated to enlarge the lumen of the blood vessel to its original diameter. Simultaneously, a drug may be transferred to the vessel wall to prevent early and late re-narrowing due to hyperproliferation of the injured vessel wall.

Medical devices may contain drugs either to improve the tolerance, efficacy or in vivo life-time of the device or the device serves as carrier for the drug. In any case the dose density (e.g. mg drug/mg device or mg drug/mm device surface), chemical stability, adherence, release rate, and total amount released are important and frequently critical features of the drug formulation. These properties are the more critical the more the requirements during production and application of the device vary or may even be contradictory. Drug-coated angioplasty catheters are typical examples: the drug coating must adhere firmly to tolerate mechanical stress during production including folding of balloons, crimping of stents, packaging, transportation to customers, and during final application, which involves the passage through a narrow hemostatic valve, an introductory sheath or guiding catheter and a variable distance through possibly tortuous and narrow blood vessels. When the balloon is inflated the drug should be released within a minute or less as rapidly and as completely as possible. The problem was demonstrated by Cremers et al (Cremers B, Biedermann M, Mahnkopf D, Bdhm M, Scheller B. Comparison of two different paclitaxel-coated balloon catheters in the porcine coronary restenosis model. Clin Res Cardiol 2009; 98:325-330) who retrieved as much as 50% of the dose from balloons after expansion for one minute in coronary arteries of pigs, whereas other catheters coated with the same drug and dose but in a different formulation released more than 95%. Almost perfect results (i.e., loss of only 10% of dose and residual drug on the balloon after expansion in an artery of about 10%) were achieved with a rigid prototype balloon (Scheller B, Speck U, Abramjuk C, Bernhardt U, Bohm M, Nickenig G. Paclitaxel balloon coating—a novel method for prevention and therapy of restenosis. Circulation 2004; 110: 810-814). The application of the same coating composition to more flexible modern balloon catheters resulted in problems, i.e., larger premature loss of the drug. The coating of scoring or cutting balloons with drugs in a reliable way with a dose which is sufficient to be efficacious imposes additional problems because of the more complex structure of the device and the more complex production process.

2. Prior Art

Protection from premature drug release. Premature release of a drug from a balloon is a major problem which has been addressed by a variety of methods. Some of them are mechanical, e.g. the use of protection tubes, sleeves, envelops. Examples are U.S. Pat. No. 5,370,614, U.S. Pat. No. 6,306,166, and U.S. Pat. No. 6,616,650 disclosing various protective sheaths which are retracted before the balloon is inflated, or U.S. Pat. No. 6,419,692 proposing a cover which bursts during balloon expansion. A different approach is taken in U.S. Pat. No. 5,893,840 disclosing structured balloon membranes with tiny cavities, WO 94/23787 with roughened balloon membranes to enhance the adherence of coating, or more recently U.S. Pat. No. 7,108,684 proposing a pouch which protects the drug-containing layer on the balloon and WO 2009/066330 disclosing methods placing the drug selectively under the folds of a folded balloon. Although efficacious these methods have the disadvantage of increasing the complexity and cost of production or make handling of the devices more difficult or add to the diameter of the devices (which must be kept as small as possible to facilitate passage through stenotic lesions). In some embodiments the protective membranes or perforated membranes interfere with the scoring components of the balloons or prevent a homogeneous transfer of the drug to the tissue or even put the patient at risk. None of these methods has been applied to scoring or cutting balloons and nothing is known about problems which will arise from the increasing complexity and mechanical problems or from a disturbance of the protecting envelops by the scoring or cutting structures and vice versa.

Other approaches use either physical or chemical methods to control the release of drugs from a balloon surface, e.g. U.S. Pat. No. 5,304,121 describes a hydrogel which releases the drug only after exposure to a triggering agent; U.S. Pat. No. 5,199,951 relies on thermal activation; according to U.S. Pat. No. 7,445,792 a lipophilic "hydration inhibitor" protects water-soluble drugs from premature release; and according to U.S. Pat. No. 5,370,614 a viscous matrix protects the drug from premature release, however, the viscous matrix must be protected by a sheath during the passage to the stenotic vessel segment. None of the methods has been tested in practice and proven to fulfill the requirements for fast, reliable and complete drug transfer to the target tissue. None of the methods has been designed to be used with scoring or cutting balloons.

Numerous methods of sustained drug release are known and successfully used in practice but are not applicable to medical devices which are in contact with the target tissue for only a few seconds or minutes. Sustained drug release is usually achieved by embedding the drug in a polymer which restricts the diffusion rate to the surface and in this way controls the transfer into the adjacent tissue.

Therefore, a need remains for a method or formulation which protects the coating from premature losses during production, handling, and on the way to the lesion and still allows the immediate and complete release of the active ingredient at a location and point in time determined by the user. During the production process this problem is even more severe for scoring and cutting balloons because of the more complex structure of the product. Scoring and cutting balloons have merits in the treatment of certain lesions, e.g. if the conventional smooth balloons tend to dislocate during inflation or if a controlled and predetermined injury of the vessel wall is preferred to an uncontrolled dissection during balloon inflation. Nevertheless, the problem of renarrowing of the vessel lumen due to excessive neointimal proliferation as a reaction to the unavoidable injury during dilatation is the same as with conventional balloon catheters.

An advantageous way to control adherence and release of a drug from a medical device, e.g., an angioplasty balloon, is the selection of a suitable formulation and coating which do not require mechanical protection, or additional physical or chemical interaction with the coating except the usual operation of the device e.g. inflation of a folded balloon to induce the release of the drug. Although desirable and frequently tried, the conflicting objectives of perfect adherence during production and before use and immediate release at the site of action make it a difficult task. A large variety of patent applications vaguely disclose measures, compositions and devices to solve this problem for conventional balloon catheters either by the selection of drugs, the choice of specific coating processes or formulations containing various additives. Long lists of compounds have been copied from textbooks of chemistry, pharmacology, or pharmacy but even with extensive experimentation disclosures are not sufficiently clear to allow a person familiar with the subject and skilled in the art to come to a satisfactory solution without an inventive step. Examples of prior art are US 2008/0118544 reciting an excessive number of substances and substance classes or U.S. Pat. No. 7,445,795 which discloses the use of "hydration inhibitors" not applicable to the preferred class of very lipophilic drugs which require "hydration enhancers" or "dispersion and dissolution enhancers" as, e.g., disclosed in WO 2004/028582. Although the hydrophilic additives (which may be regarded as "hydration enhancers") work quite well on certain conventional balloon membranes (Scheller B, Speck U, Abramjuk C, Bernhardt U, Bohm M, Nickenig G. Paclitaxel balloon coating—a novel method for prevention and therapy of restenosis. Circulation 2004; 110: 810-814) the adherence to various modern conventional or scoring PTA or PTCA balloons is either too weak or too tight resulting in premature loss of a major proportion of the drug or incomplete release at the target site. None of the known compositions has been tried on scoring or cutting balloon catheters.

Antioxidants.

In theory, antioxidants address an almost universal feature of diseased tissue, namely the "reactive oxygen species", and should have widespread medical applications. In practice, only very few controlled clinical trials have shown beneficial effects of antioxidants (Suzuki K. Antioxidants for therapeutic use: Why are only a few drugs in clinical use? Advanced Drug Delivery Reviews 2009; 61:287-289). Antioxidants are mentioned as potentially useful drugs for the treatment of focal vascular disease such as stenosis, restenosis, atherosclerotic plaques, and vulnerable plaques in US 2009/0136560 with no additive, in U.S. Pat. No. 5,571,523 as agents inducing apoptosis in vascular smooth muscle cells, in WO 2004/022124 either as active drugs or as Ahydration inhibitors'. In US 2008/0241215 probucol, a drug approved for the treatment of hyperlipidemia, a known risk factor for atherosclerosis, is proposed as the active ingredient in stent coating, either alone or combined with rapamycin or another anti-restenotic agent in a slow-release formulation. U.S. Pat. No. 6,211,247 claims pharmaceutical compositions containing an effective dose of resveratrol for preventing or treating various vascular pathologies following coronary interventions. Similarly, US 2007/0037739 discloses local delivery systems comprising various bioactive agents including resveratrol which either alone or in the specified combinations are suitable for treating or preventing abnormal luminal cell proliferation. None of the above-mentioned documents contains data encouraging the use as additives to a lipophilic drug to delay the release rate of the drug and no specific compositions are disclosed which address the above-mentioned problems of adhesion of a drug before the target lesion is reached and immediate release when required.

Small proportions of antioxidants are commonly used to protect drugs or nutrients from decomposition by oxygen or oxidation, an application which has also been proposed for drugs coated on implantable medical devices such as stents (US 2007/0020380, US 2009/0246253) or balloon catheters (US 2005/003 7048, US 2009/0246252, especially paragraph [105]). However, antioxidants are commonly used in proportions of less than 1% by weight in relation to 100% by weight of the drug. Normally it is intended to use as less antioxidant as possible, i.e., less than 0.1% by weight in relation to 100% by weight of the drug (Voigt R. Lehrbuch der phar-mazeutischen Technologie. 5. Edition, Verlag Chemie, Weinheim—Deerfield Beach, Florida—Basel, 1984). US 2005/0037048 discloses a specific example which refers to a selected drug in a polymeric matrix requiring an unusually high proportion of antioxidant.

Again, none of the above mentioned documents provides any hint to an advantage in using antioxidants in combination with stable (i.e. oxidation-resistant drugs) and/or at dose levels which provide no therapeutic or prophylactic action.

Present Invention.

The problem underlying the present invention was the provision of a scoring or cutting balloon catheter with an improved adherence of the drug without negative effect on the release of the drug at the target site.

The problem was solved by a scoring or cutting balloon catheter according to claim 1. In other words, the problem was solved by a scoring or cutting balloon catheter carrying at least on a portion of its surface at least one oxidation-insensitive drug or oxidation-insensitive polymer-free drug preparation and at least one lipophilic antioxidant at a ratio of 3-100% by weight of the at least one lipophilic antioxidant in relation to 100% by weight of the drug, wherein the at least one oxidation-insensitive drug is selected of taxanes, thalidomide, statins, corticoids and lipophilic derivatives of corticoids, and the at least one lipophilic antioxidant is selected of nordihydroguaiaretic acid, resveratrol and propyl gallate. "Polymer-free" means that no additional polymer is part of the coating. Preferred embodiments are disclosed in the dependant claims. Usually, antioxidants are used to stabilize oxidation-sensitive drugs against degradation by oxygen. They are considered useless in this regard if the drug is stable against oxidative degradation, i.e. if the drug is oxidation-insensitive. Below, the terms "oxidation-insensitive drug", "active drug" and "drug" are used interchangeable all meaning an oxidation-insensitive drug if the invention is concerned.

During testing of a large variety of coating methods, additives and drug combinations the surprising discovery was made that certain lipophilic antioxidants added to less or even more lipophilic and more or less water soluble drugs, which are oxidation-insensitive, in a defined mass ratio significantly increase the adherence of the drug to scoring and cutting balloons during handling and on the way to the target lesion even if the target lesion is located far away from the site where the device first enters a blood-filled introductory sheath, guiding catheter or vessel containing During testing of a large variety of coating methods, additives and drug combinations the rapidly flowing blood. This was also tested with scoring balloons. In spite of the additional mechanical stress (as compared to conventional balloons) imposed on the coating due the movement of the scoring wires surrounding the folded balloons the loss of the drug during the passage through a narrow hemostatic valve and a curved guiding catheter was very low. Thus, at least one lipophilic antioxidant in an amount of 3-100% by weight is used as an adherence improver for drugs coated on a scoring or cutting balloon catheter during this initial step of introducing the medical device into the vasculature. The wording "at least one lipophilic antioxidant" means that single antioxidants but also mixtures of different antioxidants are included. Other substances or pharmaceutical compounds may be added to further adjust the properties of the product to the demand in respect of stability or other pharmaceutical requirements and tolerance etc.

Examples of active drugs are inhibitors of cell proliferation, preferably taxanes such as paclitaxel, docetaxel and protaxel. Alternatively, specific inhibitors of neovascularization such as thalidomide, statins like atorvastatin, cerivastatin, fluvastatin or anti-inflammatory drugs like corticoids or even more preferred lipophilic derivatives of corticoids such as betamethasone diproprionate or dexa-methasone-21-palmitate are examples of oxidation-insensitive drugs. Various drugs may be applied or combined if different pharmacological actions are required or efficacy or tolerance is to be improved. Thus, the wording "at least one drug or drug preparation" means that single drugs but also mixtures of different drugs are included. Preferred drugs are either lipophilic (partition coefficient between n-butanol and water >10, or display very poor water solubility (<1 mg/ml. 20° C.)). Preferred are those drugs which in dry state are chemically stable during long-term storage without the addition of an antioxidant, e.g., paclitaxel and other taxanes, statins, thalidomide, corticosteroids and lipophilic derivatives of corticoids. Thereof, the preferred ones are paclitaxel, protaxel and docetaxel with paclitaxel being the most preferred drug. Drugs must be used in a dose range providing the desired effect without compromising the technical features of the coated balloon (balloon catheter) such as flexibility. A preferred dose range is between 1 and 10 pg/mm2 balloon surface, most preferred up to 6 g/mm$^2$.

The lipophilic antioxidants are antioxidants which are solid at temperatures up to 40° C. Preferred are nordihydroguaiaretic acid, propyl gallate and resveratrol, more preferred nordihydroguaiaretic acid and resveratrol, most preferred only resveratrol. Probucol is not a preferred additive.

Combinations of these antioxidants with the above-mentioned drugs showed an improved adherence. Different combinations, especially with other oxidation-insensitive drugs, did not how a significantly improved adherence or required very high amounts of the antioxidant which impairs the mechanical features of the balloons (much more than 100% by weight in relation to 100% by weight of the drug).

Lipophilic antioxidant means that the partition coefficient of the antioxidant between n-butanol and water is >1, more preferred >10, and even more preferred >100.

Preferably, the drug is more lipophilic than the antioxidant, i.e., the partition coefficient between n-butanol and water of the drug is higher than the partition coefficient between n-butanol and water of the antioxidant. If, however, an excipient prevents premature loss of the drug from the medical device and/or enhances the fast and complete transfer to the tissue it shall not be excluded because of its physicochemical properties.

At the dose density used the chosen antioxidants do not display relevant therapeutic or prophylactic effects in respect of the disease which is treated by the coated medical device nor is the relative amount of the antioxidant chosen to protect the drug from oxidative decomposition. This means that a non-bioactive dose of the antioxidant is preferred. The dose density and the mass relation of the antioxidant to the drug are solely optimized in respect of adherence of the drug to and release from the medical device surface. The antioxidant dose on the medical device is too low to provide the desired pharmacological effect, i.e., it is ineffective on its own. The antioxidant on the medical device is not required to protect the active drug (e.g., the antiproliferative drug) from oxidative decomposition during production, sterilization and storage; at least it is not required at the dose or concentration applied according to this invention. "Not required" means that the active drug is stable enough without the antioxidant or at an antioxidant dose or dose density or ratio to the active drug below the dose according to the present invention. "Sufficient stability" means that less than 5% of the active drug is lost due to oxidative decomposition between the coating of the device and the use in patients one year after production if stored at ambient temperature (drug or drug preparation stable against oxidative decomposition, air-oxygen exposure not excluded). In conclusion the invention relates to a combination of an antioxidant with a drug which needs no protection from oxidative decomposition or at least a dose of the antioxidant which surpasses the amount of antioxidant required protecting the drug from oxidation by its antioxidant action. The antioxidant serves as additive or excipient not functioning as a stabilizer for an oxidation-sensitive biologically active ingredient (drug) nor displaying a therapeutic or prophylactic effect on its own at the selected dose.

The dose of the antioxidant on the surface of a medical device may be defined in respect of the therapeutic drug. Preferred relationships (weight/weight) are 3-100% antioxidant of the weight of the drug. For example, if the dose density of the drug is 5 g/mm$^2$ device surface, the amount of antioxidant is 0.15-5.0 g/mm$^2$. Higher proportions of the antioxidant may be selected if either the drug is applied at a dose below 3 pg/mm$^2$ device surface or the adherence of the drug to the device surface is further improved. The antioxidant load of the device may reach 10 g/mm$^2$. A higher load is possible. Other preferred ranges for the relationship of antioxidant to drug on a weight/weight basis are 5-100%, more preferred 10-100%, and even more preferred 20-100% and most preferred 50-100% in relation to 100% of the drug. Especially the range of 50-100% on a weight/weight basis enhances the adherence significantly (see Example 3). The relationship may also be defined in respect of moles: in a preferred embodiment the antioxidant is present from 10 mole % relative to the drug to 200 mole %.

Higher amounts of the antioxidant may be useful; they may be only excluded if they display on their own significant pharmacological prophylactic or therapeutic effects in respect of the disease to be treated.

If more than one drug is used the total weight of the drugs or the total moles of the drugs serve as basis for the calculation of the amount of the antioxidant. If more than one antioxidant is used the total weight of the antioxidants or the total moles of the antioxidants serve as basis for the calculation of the amount of the antioxidants.

Other well tolerated and approved additives and/or excipients may be applied to further improve the mechanical or pharmaceutical properties of the coating. Polymer-free coating compositions are preferred. It is a special advantage of the present compositions that they do not require the use of polymers to prevent premature release of the drug. Nevertheless, small amounts of pharmaceutically acceptable polymers such as polyacrylic acids may be added, e.g., to improve the distribution of the drug on the balloon or adherence of the dry coating during handling. Small amounts mean about 1-20% by weight in relation to 100% by weight of the drug(s). If polymers are used substances with low to moderate molecular weight, i.e., 2000 to 50,000 D are preferred.

Usually, drugs and mixtures of drugs with additives are coated on medical devices as liquid formulations in volatile solvents, according to the current invention preferably without addition of a polymer, i.e. polymer-free. The choice of solvent is important for the distribution of the drug on the device, especially if the device is coated at an advanced stage of production. An advanced stage of production of a scoring or cutting balloon may include the scoring or cutting elements of the device, the structures required to fix these elements and an already folded balloon. The solvents further determine the structure of the coating in dry state and the adherence and release of the drug from the surface. Preferred organic solvents are acetone, tetrahydrofuran, and various alcohols such as methanol and ethanol. Usually, 1 to 30% (volume/volume) water is added. The drug or drugs and the antioxidents may be applied at the same time dissolved in the same solvent or mixture of solvents. Alternatively, they may be separately dissolved in the same or different solvents and sequentially applied. The solution(s) is/are polymer-free in either case. In a preferred embodiment, the scoring or cutting balloon catheter has been polymer-free coated with at least one oxidation-insensitive drug and at least one antioxidant both together dissolved in tetrahydrofuran or a mixture of solvents containing more than 25% (v/v) tetrahydrofuran or each separately dissolved optionally selecting a different solvent for the at least one lipophilic antioxidant. Another preferred embodiment is based on a scoring or cutting balloon catheter, which has been polymer-free coated with at least one oxidation-insensitive drug and at least one antioxidant both together dissolved in acetone or a mixture of solvents containing more than 25% (v/v) acetone or each separately dissolved optionally selecting a different solvent for the at least one lipophilic antioxidant. Coating with dry particles such as micro- or nano-particles, crystals, capsules etc. or particles suspended in a liquid preparation is possible. Coating with particles may be facilitated by a roughened or sticky surface of the medical device.

A variety of coating procedures providing more or less uniform layers on medical devices are known from the literature and are disclosed in patent applications. These include simple dipping, spraying, and methods providing precise doses and homogeneous distributions (e.g., WO 2009/018816). Coating may be applied stepwise, either as multiple layers of the same composition or as layers with different compositions e.g. the drug first and the antioxidant second or in the opposite order. All these methods may be applied to the formulations of the current invention. The sequential coating with, e.g., (a) the drug first and (b) second the antioxidant dissolved in a solvent in which the drug is poorly soluble by, e.g., spraying results in substantially separate layers. This is completely different from the application of antioxidants for chemical protection of oxidation sensitive drugs which requires a homogeneous mixing of the antioxidant with the drug.

Thus, a preferred embodiment of the present invention is a scoring or cutting balloon catheter, which has been polymer-free sequentially coated with at least one oxidation-insensitive drug and at least one lipophilic antioxidant in a way that the oxidation-insensitive drug and the antioxidant are not homogeneously mixed.

Furthermore, coated scoring or cutting balloon catheter may be dried under different conditions such as temperature, air flow, gas composition, and pressure at different stages of the production process. They may be stored in water-vapor-tight seals with a separately packed water absorbing-agent within the seal.

Subject of the current invention are scoring or cutting balloon catheters, e.g., catheters for angioplasty or coronary angioplasty. Preferred are scoring or cutting balloon catheters for short-lasting use during an interventional image guided therapy. Short lasting use means that the device is not implanted but eliminated from the body when the procedure is finished, usually within less than 10 minutes, but never later than a few, preferably 5, hours after the end of the procedure. Catheters may contain balloon membranes made from various polymers and copolymers, polyamides (nylon 12, pebax), polyethylenes, polyurethanes, various polyvinyls and the like. Independently of the type of material, the adherence and release properties of drugs are improved by the addition of lipophilic antioxidants. Furthermore, catheters comprise elements which are aimed at scoring or cutting the surfaces in direct contact with the inflated balloons, e.g. wires with various profiles, or protrusions of the balloon surface.

The scoring or cutting balloon catheter carries the at least one drug or drug preparation and the at least one lipophilic antioxidant at least on a portion of its surface which is aimed at coming into close contact with the tissue to be treated, e.g., the balloon at the distal portion of a catheter shaft. This means that at least 5%, preferably more than 50%, most preferably more than 90% of the surface is coated. The balloon of a scoring or cutting balloon catheter has a central cylindrical part and two opposite conical ends. If less than 100% of the balloon catheter's surface is coated, it is preferred that the cylindrical part is coated and that at least parts of or the complete conical ends remain uncoated.

Another embodiment is a scoring or cutting balloon catheter carrying at least on a portion of its surface polymer-free at least one Limus drug or Limus drug preparation and at least one lipophilic antioxidant, which is nordihvdroguaiaretic acid or resveratrol, preferably resveratrol, at a ratio of 3-100% by weight of the at least one lipophilic antioxidant in relation to 100% by weight of the drug.

Preferably, the Limus drug is an mTOR inhibitor, more preferably selected from sirolimus, everolimus, zotarolimus, biolimus and temsirolimus, most preferred sirolimus. Concerning preferred ways of carrying out this embodiment, the same applies as described above with respect to the combination of oxidation-insensitive drugs/drug preparations and lipophilic antioxidants.

Below, the invention is described by means of Examples.

EXAMPLE 1

Balloons for percutaneous transluminal coronary angioplasty type A (AngioSculpt 3.5-20 mm, AngioScore, Inc., Fremont Calif., USA) were coated either with aclitaxel alone or combined with iopromide (iodinated contrast agent according to WO 02/076509) or different amounts of butylated hydroxy-toluene (BHT); solvent: acetone/ethanol/H2O. Coated balloons were tested in respect of paclitaxel loss during the passage through a hemostatic valve, Medtronic Launcher JL 3.5 6F guiding catheter and one minute in stirred blood (37° C.). When admixed at sufficient concentration to the coating solution, BHT improved the adhesion of paclitaxel.

| Coating solution | Catheter Labeling | Loss on the way to the lesion % of dose |
|---|---|---|
| No additive | 1 | 24 |
|  | 2 | 40 |
| Iopromide as an additive; ca. 0.5 mg/mg paclitaxel | 3 | 49 |
|  | 4 | 34 |
| BHT 5% = 0.05 mg BHT/mg paclitaxel | 5 | 15 |
|  | 6 | 26 |
| BHT 24% = 0.24 mg BHT/mg paclitaxel | 7 | 10 |
|  | 8 | 6 |

EXAMPLE 2

Balloons for percutaneous transluminal coronary angioplasty type A were coated either with paclitaxel alone or combined with iopromide (iodinated contrast agent according to WO 02/076509), see example 2, or butylated hydroxytoluene (BHT) or nordihydroguaiaretic acid.

Coated balloons were tested in respect of paclitaxel loss during the passage through a hemostatic valve, a Medtronic Launcher JL 3.5 6F guiding catheter and in stirred blood (37° C.) for one minute. When admixed at sufficient concentration to the coating solution, lipophilic antioxidants improve the adhesion of paclitaxel whereas the release during balloon inflation in a coronary artery (determined in separate experiments) was not impaired.

| Coating solution | Labeling | Loss on the way to the lesion % of dose | Residual paclitaxel on balloons % of dose |
|---|---|---|---|
| No additive acetone/ethanol/H2O | Control 1, 2 | 32 | No data |
| Iopromide as an additive; ca. 0.5 mg/mg paclitaxel; acetone/ethanol/H2O | Control 3, 4 | 42 | ~10 |
| BHT 24% = 0.24 mg BHT/mg paclitaxes; acetone/ethanol/H2O | A | 15.3 ± 9.5 | 11 |
| BHT 24% = 0.24 mg BHT/mg paclitaxes; tetrahydrofuran/ethanol/H2O | B | 3.4 ± 4.8 | 13 |
| Nordihydroguaiaretic acid 35% = 0.35 mg/mg paclitaxel; acetone/ethanol/H2O | C | 4.2 ± 7.2 | No data |

EXAMPLE 3

Balloons for percutaneous transluminal coronary angioplasty type A were coated either with paclitaxel without resveratrol or combined with resveratrol. Coated balloons were tested in respect of paclitaxel loss as described in example 1. When admixed at sufficient concentration to the coating solution, resveratrol improved the adhesion of paclitaxel.

| Coating solution | Labeling | Loss on the way to the lesion % of dose |
|---|---|---|
| Resveratrol 0% acetaone/tetrahydrofuran/H2O | Control | 25 ± 8 |
| Resveratrol 20% = 0.2 mg/mg paclitaxel; acetone/tetrahydrofuran/H2O | N | 21 ± 6 |
| Resveratrol 50% = 0.5 mg/mg paclitaxel; acetone/tetrahydrofuran/H2O | O | 7 ± 11 |

EXAMPLE 4

Balloons for percutaneous transluminal coronary angioplasty type A were coated in already folded condition either with paclitaxel without or with polyacrylic acid. Polyacrylic olyacrylic acid (molecular weight about 6000 D (Polysciences Inc., USA) and glycerol improved the homogeneity of the coating on the balloon.

| Coating solution | Labeling | Distribution on balloons |
|---|---|---|
| Paclitaxel without polyacrylic acid acetone/tetrahydrofuran/H2O | N | Spreading limited to directly accessible surface |
| 0.8 mg polyacrylic acid + 0.06 mg glycerol/mg paclitaxel acetone/tetrahydrofuran/H2O | D | Irregular distribution, partly below the folds |
| 0.15 mg polyacrylic acid + 0.06 mg glycerol/mg paclitaxel in acetone/tetrahydrofuran/H2O | E | Almost homogeneous distribution including areas below the folds |

What is claimed is:

1. A balloon catheter for angioplasty or coronary angioplasty comprising:
a shaft having a proximal portion and a distal portion;
an inflatable balloon coupled to the distal portion of the shaft;
a nonimplantable scoring structure surrounding the balloon, wherein the scoring structure is capable of scoring a luminal surface of a blood vessel upon inflation of the inflatable balloon;
wherein the balloon catheter carries on at least on a portion of its surface a therapeutically effective amount of at least one oxidation-insensitive drug and an amount of a lipophilic antioxidant that will protect the drug from premature loss during delivery to the angioplasty site and that is 3-100% by weight of the drug, wherein the at least one oxidation-insensitive drug is selected from the group consisting of: taxanes, thalidomide, statins, corticoids and lipophilic derivatives of corticoids, and the lipophilic antioxidant is nordihydroguaiaretic acid.

2. The balloon catheter according to claim 1, wherein the scoring structure comprises one or more wires capable of scoring the luminal surface upon inflation of the inflatable balloon.

3. The balloon catheter according to claim 1, wherein the oxidation-insensitive drug is a taxane selected from the group consisting of paclitaxel, protaxel and docetaxel.

4. The balloon catheter according to claim 3, wherein the taxane is paclitaxel.

5. The balloon catheter according to claim 1, wherein the ene antioxidant load is up to 10 μg/mm² of coated catheter surface and the antioxidant is provided at a dose level that provides no therapeutic or prophylactic effect.

6. The balloon catheter according to claim 1, wherein the lipophilic antioxidant is contained at a ratio of 20-100% by weight, in relation to 100% by weight of the at least one oxidation-insensitive drug.

7. The balloon catheter according to claim 1, wherein the lipophilic antioxidant is contained at a ratio of 50-100% by weight, in relation to 100% by weight of the at least one oxidation-insensitive drug.

8. The balloon catheter according to claim 1, further comprising a coating composition including the therapeutically effective amount of at least one oxidation-insensitive drug and an amount of lipophilic antioxidant, wherein the coating composition is polymer-free.

9. A balloon catheter for angioplasty or coronary angioplasty comprising:
a shaft having a proximal portion and a distal portion;
an inflatable balloon coupled to the distal portion of the shaft;
a nonimplantable cutting structure surrounding the balloon, wherein the cutting structure is capable of cutting a luminal surface of a blood vessel upon inflation of the inflatable balloon;
wherein the balloon catheter carries on at least on a portion of its surface a therapeutically effective amount of at least one oxidation-insensitive drug and an amount of a lipophilic antioxidant that will protect the drug from premature loss during delivery to the angioplasty site and that is 3-100% by weight of the drug, wherein the at least one oxidation-insensitive drug is selected from the group consisting of: taxanes, thalidomide, statins, corticoids and lipophilic derivatives of corticoids, and the lipophilic antioxidant is nordihydroguaiaretic acid.

10. The balloon catheter according to claim 9, wherein the at least one drug comprises oxidation-insensitive paclitaxel.

11. A balloon catheter for angioplasty or coronary angioplasty comprising:
a shaft having a proximal portion and a distal portion;
an inflatable balloon coupled to the distal portion of the shaft, wherein the inflatable balloon comprises a surface, wherein at least a portion of the surface carries a therapeutically effective amount of an oxidation-insensitive taxane drug and an amount of nordihydroguaiaretic acid that protects the oxidation-insensitive taxane drug from premature loss during delivery to an angioplasty site, wherein the nordihydroguaiaretic acid is at a ratio of 20-100% by weight, in relation to 100% by weight of the oxidation-insensitive taxane drug; and
a nonimplantable scoring structure surrounding the balloon, wherein the nonimplantable scoring structure is capable of scoring a luminal surface of a blood vessel upon inflation of the inflatable balloon.

12. The balloon catheter according to claim 11, wherein the scoring structure comprises one or more wires capable of scoring the luminal surface upon inflation of the inflatable balloon.

13. The balloon catheter according to claim 11, wherein the oxidation-insensitive taxane drug is selected from the group consisting of paclitaxel, protaxel and docetaxel.

14. The balloon catheter according to claim 13, wherein the taxane is paclitaxel.

15. The balloon catheter according to claim 11, wherein the nordihydroguaiaretic acid load comprises up to 10 µg/mm$^2$ of coated catheter surface.

* * * * *